(12) United States Patent
Jonaitis et al.

(10) Patent No.: US 11,866,420 B2
(45) Date of Patent: Jan. 9, 2024

(54) HYDROCHLORIDE SALT FORMS OF A SULFONAMIDE STRUCTURED KINASE INHIBITOR

(71) Applicant: Aurigene Oncology Limited, Karnataka (IN)

(72) Inventors: David Jonaitis, Brookston, IN (US); Oskari Karjalainen, Helsinki (FI)

(73) Assignee: Aurigene Oncology Limited, Karnataka (IN)

( * ) Notice: Subject to any disclaimer, the term of this patent is extended or adjusted under 35 U.S.C. 154(b) by 341 days.

(21) Appl. No.: 17/273,774

(22) PCT Filed: Sep. 5, 2019

(86) PCT No.: PCT/FI2019/050629
§ 371 (c)(1),
(2) Date: Mar. 5, 2021

(87) PCT Pub. No.: WO2020/049217
PCT Pub. Date: Mar. 12, 2020

(65) Prior Publication Data
US 2021/0332028 A1    Oct. 28, 2021

(30) Foreign Application Priority Data
Sep. 6, 2018 (FI) .................................. 20185743

(51) Int. Cl.
*C07D 403/04* (2006.01)

(52) U.S. Cl.
CPC ........ *C07D 403/04* (2013.01); *C07B 2200/13* (2013.01)

(58) Field of Classification Search
CPC . C07D 403/04; C07B 2200/13; C07C 403/04; A61K 31/4184
See application file for complete search history.

(56) References Cited

FOREIGN PATENT DOCUMENTS

| JP | 2014-528469 A | 10/2014 | |
| WO | WO 2013/053983 A1 | 4/2013 | |
| WO | WO-2018172616 A1 * | 9/2018 | ........... C07D 403/04 |

OTHER PUBLICATIONS

Targeting FGFR Signaling in Cancer Clin Cancer Res; 2015, 21(12), 2684-2694 (Year: 2015).*
N. Duggirala et al., 52 Chem. Commun., 640-655 (2016) (Year: 2016).*
Mino R. Caira, "Crystalline Polymorphism of Organic Compounds," Topics in Current Chemistry, Springer, Berlin, vol. 198, Jan. 1, 1998, pp. 163-208.
International Search Report, issued in corresponding International Application No. PCT/FI2019/050629 from the European Patent Office, dated Oct. 29, 2019, 2 pages.
Anderson et al., The Practice of Medicinal Chemistry. Camille Georges Wermuth (Ed.). pp. 347-365, Sep. 25, 1999.
Ashizawa, Machibushi pseudocrystalline polymorph (hydrate/solvate). Examination of salts and crystal forms, drug substance and formulation research, Chapter 9. Marubo Planet Co., Ltd. pp. 273, 278, 305-317, (2002).
Kawaguchi et al., Drug and crystal polymorphism. Journal of Human Environmental Engineering. 2002;4 (2):310-317.
Japanese Office Action for Application for Application No. 2021-512769, dated Aug. 22, 2023, 9 pages.

* cited by examiner

*Primary Examiner* — Brandon J Fetterolf
*Assistant Examiner* — Frank S. Hou
(74) *Attorney, Agent, or Firm* — McCarter & English, LLP; Steven G. Davis; Wei Song

(57) ABSTRACT

The present invention relates to novel hydrochloride salt forms of N-(2',4'-difluoro-5-(5-(1-methyl-1H-pyrazol-4-yl)-1H-benzo[d]imidazol-1-yl)-[1,1'-biphenyl]-3-yl)cyclopropanesulfonamide (I). Compound (I) is a selective inhibitor of FGFR/VEGFR kinase families and is useful in the treatment of cancer.

14 Claims, 3 Drawing Sheets

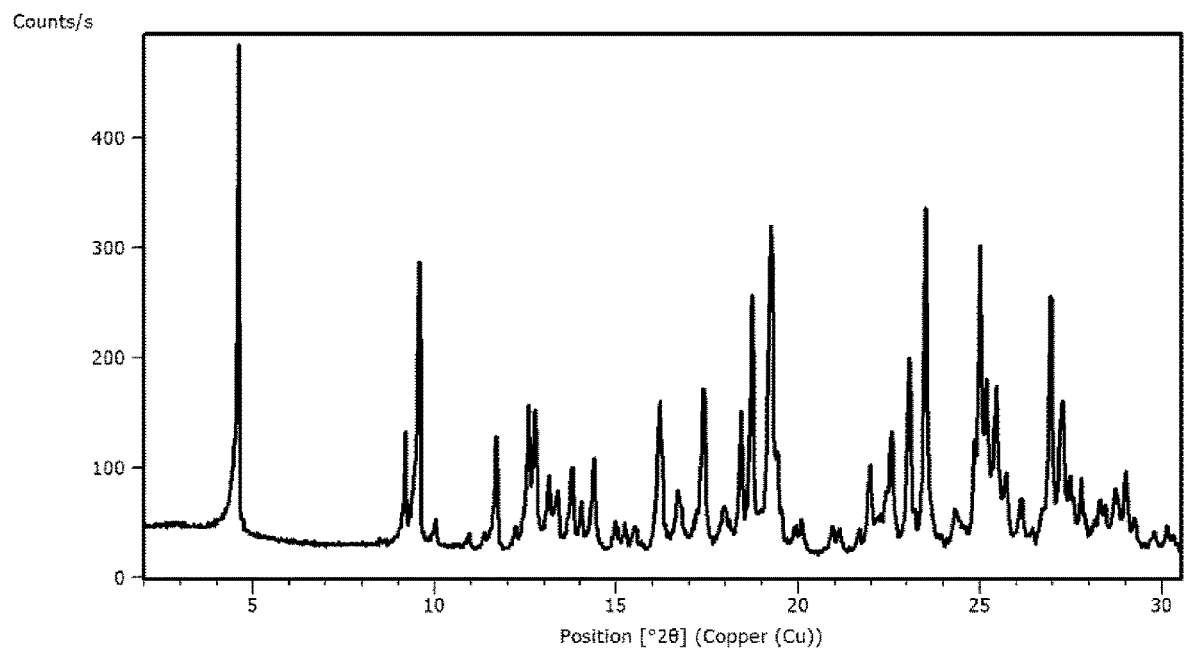
FIG. 1. Form 1 XRPD
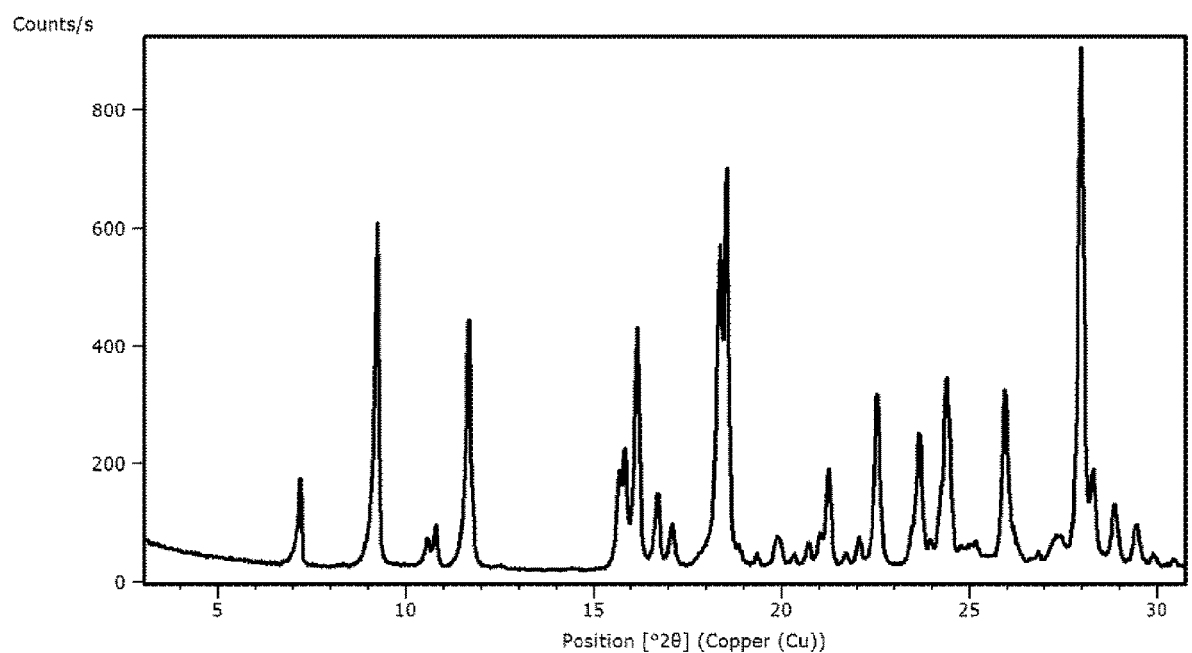
FIG. 2. Form 3 XRPD

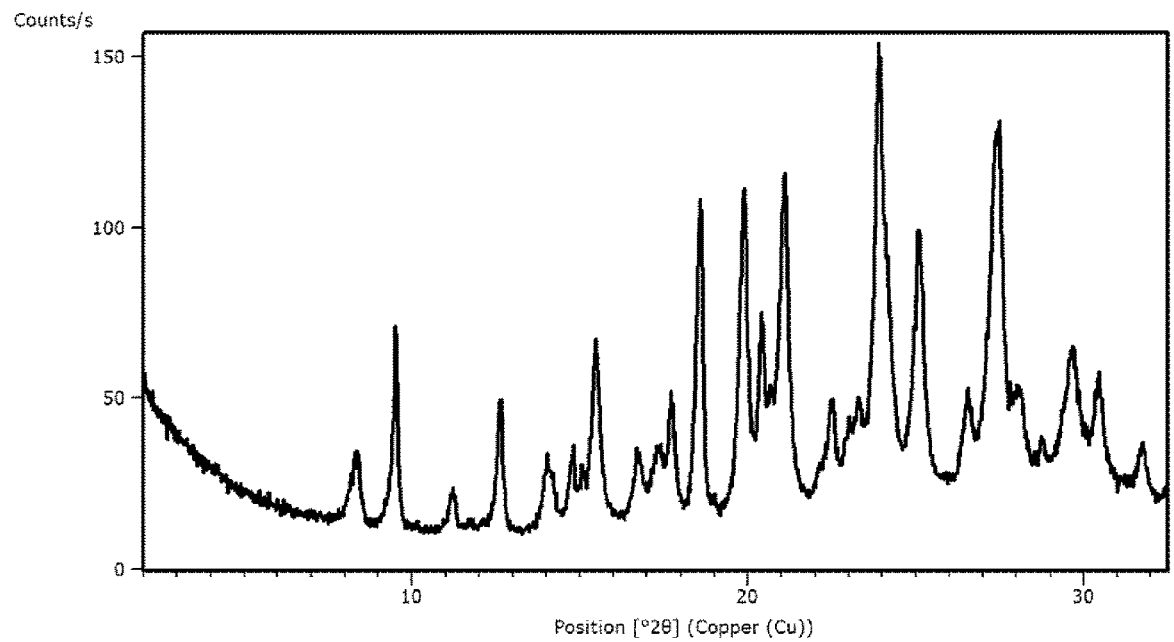
FIG. 3. Form 5 XRPD
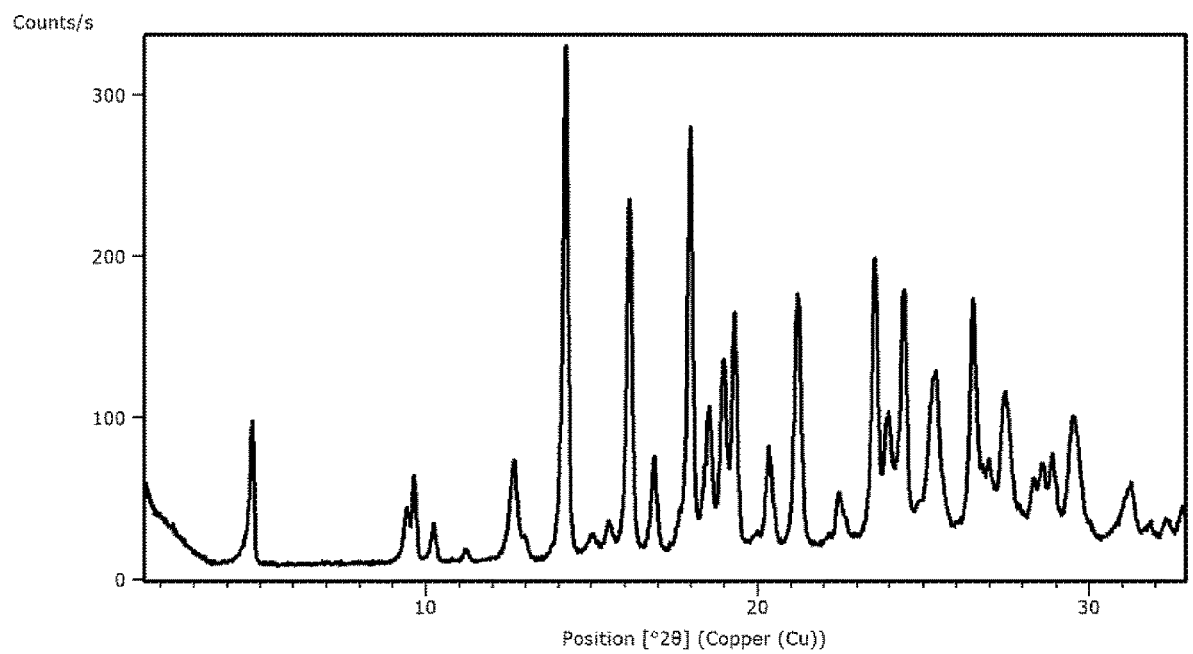
FIG. 4. Form 8 XRD

HYDROCHLORIDE SALT FORMS OF A SULFONAMIDE STRUCTURED KINASE INHIBITOR

This is a national stage application under 35 U.S.C. § 371 of International Patent Application No. PCT/FI2019/050629, filed Sep. 5, 2019, which claims the benefit of priority of Finnish Patent Application No. 20185743, filed Sep. 6, 2018, both of which are incorporated herein by reference.

TECHNICAL FIELD

The present invention relates to novel hydrochloride salt forms of N-(2',4'-difluoro-5-(5-(1-methyl-1H-pyrazol-4-yl)-1H-benzo[d]imidazol-1-yl)-[1,1'-biphenyl]-3-yl)cyclopropanesulfonamide (I) and to preparation thereof. Furthermore, the invention relates to pharmaceutical compositions comprising such novel salt forms.

BACKGROUND OF THE INVENTION

The compound N-(2',4'-difluoro-5-(5-(1-methyl-1H-pyrazol-4-yl)-1H-benzo[d]imidazol-1-yl)-[1,1'-biphenyl]-3-yl)cyclopropanesulfonamide of formula (I) and derivatives thereof have been disclosed in WO 2013/053983. Compound of formula (I) is a selective inhibitor of FGFR/VEGFR kinase families and is useful in the treatment of various cancers, particularly those in which abnormal FGFR signaling has been reported, such as multiple myeloma, gastric cancer, endometrial cancer, prostate cancer, breast cancer, cholangiocarcinoma and uroepithelial carcinoma.

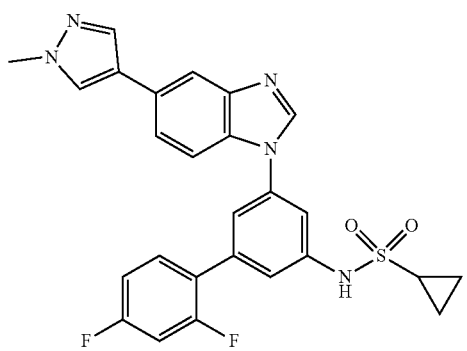

(I)

Compound (I) is practically insoluble in water at physiological pH range and has very low bioavailability after oral administration. It is also poor salt former and appears to be neutral within the physiological pH range. Salt preparation with various acids such as citric, L-malic, methanesulfonic, succinic and L-tartaric acid, and bases such as potassium hydroxide, sodium hydroxide, L-arginine and magnesium acetate was attempted. However, either the salt was not formed at all or it was chemically or physically unstable. Therefore, salt formation did not appear a promising approach for developing a stable pharmaceutical product for oral administration of compound (I) with improved bioavailability.

SUMMARY OF THE INVENTION

It has now been found that compound (I) can exist in hydrochloride salt forms which are suitable for use in the manufacture of stable pharmaceutical products and which exhibit enhanced water solubility and significantly improved bioavailability after oral administration. In particular, crystalline polymorphic forms of hydrochloride salt were found which are chemically and physically stable under various manufacture and storage conditions, have low hygroscopicity, can be obtained in consistent manner and which are not in the form of organic solvates making them particularly suitable as pharmaceutical ingredients.

Thus, in one aspect, the present invention provides hydrochloride salt of N-(2',4'-difluoro-5-(5-(1-methyl-1H-pyrazol-4-yl)-1H-benzo[d]imidazol-1-yl)-[1,1'-biphenyl]-3-yl)cyclopropanesulfonamide (I).

In another aspect, the present invention provides crystalline hydrochloride salt of N-(2',4'-difluoro-5-(5-(1-methyl-1H-pyrazol-4-yl)-1H-benzo[d]imidazol-1-yl)-[1,1'-biphenyl]-3-yl)cyclopropanesulfonamide (I).

In another aspect, the present invention provides hydrochloride salt of N-(2',4'-difluoro-5-(5-(1-methyl-1H-pyrazol-4-yl)-1H-benzo[d]imidazol-1-yl)-[1,1'-biphenyl]-3-yl)cyclopropanesulfonamide (I) in crystalline form 1.

In another aspect, the present invention provides hydrochloride salt of N-(2',4'-difluoro-5-(5-(1-methyl-1H-pyrazol-4-yl)-1H-benzo[d]imidazol-1-yl)-[1,1'-biphenyl]-3-yl)cyclopropanesulfonamide (I) in crystalline form 3.

In another aspect, the present invention provides hydrochloride salt of N-(2',4'-difluoro-5-(5-(1-methyl-1H-pyrazol-4-yl)-1H-benzo[d]imidazol-1-yl)-[1,1'-biphenyl]-3-yl)cyclopropanesulfonamide (I) in crystalline form 5.

In another aspect, the present invention provides hydrochloride salt of N-(2',4'-difluoro-5-(5-(1-methyl-1H-pyrazol-4-yl)-1H-benzo[d]imidazol-1-yl)-[1,1'-biphenyl]-3-yl)cyclopropanesulfonamide (I) in crystalline form 8. In another aspect, said crystalline form 8 is in the form of a monohydrate.

In another aspect, the present invention provides any of the above compounds for use in the treatment of cancer characterized by abnormal FGFR signalling, particularly multiple myeloma, gastric cancer, endometrial cancer, prostate cancer, breast cancer, cholangiocarcinoma and uroepithelial carcinoma.

In still another aspect, the present invention provides a method for the treatment of cancer characterized by abnormal FGFR signalling, particularly multiple myeloma, gastric cancer, endometrial cancer, prostate cancer, breast cancer, cholangiocarcinoma and uroepithelial carcinoma, comprising administering to a subject in need thereof a therapeutically effective amount of any of the above compounds.

BRIEF DESCRIPTION OF THE DRAWINGS

FIG. 1 shows the X-ray powder diffraction pattern of the crystalline form 1 of hydrochloride salt of compound (I) obtained in Example 1.

FIG. 2 shows the X-ray powder diffraction pattern of the crystalline form 3 of hydrochloride salt of compound (I) obtained in Example 2.

FIG. 3 shows the X-ray powder diffraction pattern of the crystalline form 5 of hydrochloride salt of compound (I) obtained in Example 3.

FIG. 4 shows the X-ray powder diffraction pattern of the crystalline form 8 of hydrochloride salt of compound (I) obtained in Example 4.

DETAILED DESCRIPTION OF THE INVENTION

Figure 5:
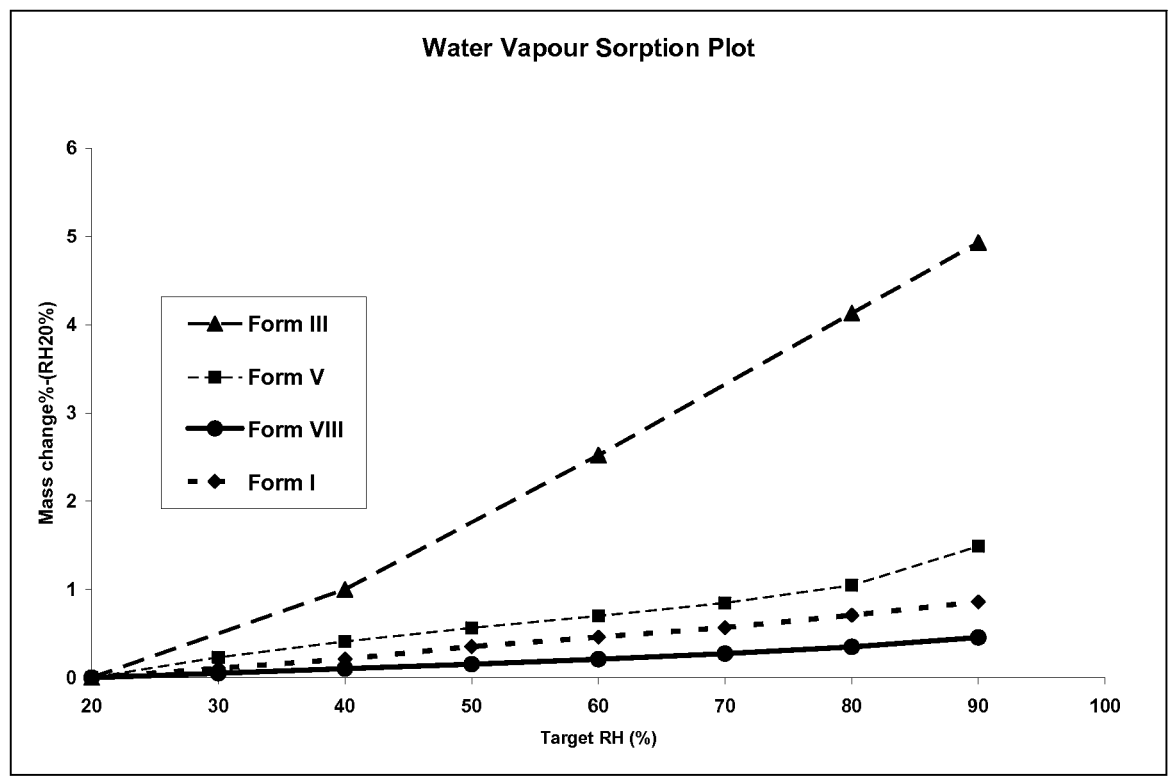

The present invention provides hydrochloride salt of N-(2',4'-difluoro-5-(5-(1-methyl-1H-pyrazol-4-yl)-1H- benzo[d]imidazol-1-yl)-[1,1'-biphenyl]-3-yl)cyclopropanesulfonamide (I). In particular, the present invention provides hydrochloride salt of compound (I) in crystalline form.

Crystalline forms 1, 3, 5 and 8 of hydrochloride salt of compound (I) have been characterized by X-ray powder diffraction (XRPD) studies.

Accordingly, in one aspect, the present invention provides crystalline form 1 of hydrochloride salt of compound (I) having a X-ray powder diffraction pattern comprising characteristic peaks at about 4.6, 9.6, 18.7, 19.2, 23.5, 25.0 and 26.9 degrees 2-theta.

In another aspect, the present disclosure provides crystalline form 3 of hydrochloride salt of compound (I) having a X-ray powder diffraction pattern comprising characteristic peaks at about 7.2, 9.2, 11.6, 16.1, 18.5, 25.9 and 27.9 degrees 2-theta.

In another aspect, the present disclosure provides crystalline form 5 of hydrochloride salt of compound (I) having a X-ray powder diffraction pattern comprising characteristic peaks at about 8.3, 9.5, 18.5, 19.8, 21.1, 23.9, 25.1 and 27.4 degrees 2-theta.

In another aspect, the present disclosure provides crystalline form 8 of hydrochloride salt of compound (I) having a X-ray powder diffraction pattern comprising characteristic peaks at about 4.7, 14.2, 16.1, 18.0, 21.2, 23.5 and 26.5 degrees 2-theta. In another aspect, said crystalline form 8 is in the form of a monohydrate.

In yet another aspect, the present disclosure provides crystalline form 1 of hydrochloride salt of compound (I) having a X-ray powder diffraction pattern comprising characteristic peaks at about 4.6, 9.6, 11.6, 12.6, 14.4, 16.2, 17.4, 18.7, 19.2, 22.5, 23.1, 23.5, 25.0, 26.9 and 27.2 degrees 2-theta. In a further aspect, the crystalline form 1 is further characterized by a X-ray powder diffraction pattern as depicted in FIG. 1.

In yet another aspect, the present disclosure provides crystalline form 3 of hydrochloride salt of compound (I) having a X-ray powder diffraction pattern comprising characteristic peaks at about 7.2, 9.2, 11.6, 15.8, 16.1, 18.5, 21.2, 22.5, 23.6, 24.4, 25.9 and 27.9 degrees 2-theta. In a further aspect, the crystalline form 3 is further characterized by a X-ray powder diffraction pattern as depicted in FIG. 2.

In yet another aspect, the present disclosure provides crystalline form 5 of hydrochloride salt of compound (I) having an X-ray powder diffraction pattern comprising characteristic peaks at about 8.3, 9.5, 12.6, 14.0, 15.5, 17.7, 18.5, 19.8, 20.4, 21.1, 23.9, 25.1, 27.4 and 29.6 degrees 2-theta. In a further aspect, the crystalline form 5 is further characterized by a X-ray powder diffraction pattern as depicted in FIG. 3.

In yet another aspect, the present disclosure provides crystalline form 8 of hydrochloride salt of compound (I) having an X-ray powder diffraction pattern comprising characteristic peaks at about 4.7, 9.4, 14.2, 16.1, 16.9, 18.0, 18.5, 19.0, 21.2, 23.5, 24.0, 24.4, 25.3, 26.5, 27.5 and 29.5 degrees 2-theta. In a further aspect, the crystalline form 8 is further characterized by a X-ray powder diffraction pattern as depicted in FIG. 4. In yet another aspect, the crystalline form 8 is a monohydrate.

XRPD measurements were performed with the X-ray powder diffractometer PANalytical X'Pert PRO at room temperature using copper filled X-ray tube (45 kV×40 mA) as the X-ray source, a fixed 1° anti-scatter slit, a programmable divergence slit with 10 mm irradiated length, and the real time multiple strip detector X'Celerator. Data collection was done in 0.017° steps at a scan speed of 0.1°/s in the range of 3–40° 2θ.

The above crystalline forms of hydrochloride salt of compound (I) are typically obtained as solvated form (hydrates). The water content of the crystalline forms may vary in different ratios depending on the conditions applied. Thus, each crystalline form can incorporate either stoichiometric or non-stoichiometric amounts of water molecules within its lattice structure. The crystalline form may comprise up to 5 molecules of water per molecule of hydrochloride salt of compound (I), appearing in different hydrated states including hemihydrate, monohydrate, dihydrate and trihydrate crystals, intermediate hydrates crystals, and mixtures thereof. In particular, the ratio may range from about 0.5 to about 5 molecules of water per 1 molecule of hydrochloride salt of compound (I), more in particular from about 1 to about 3 molecules of water per 1 molecule of hydrochloride salt of compound (I).

The crystalline form 1 of hydrochloride salt of compound (I) can be suitably prepared by contacting compound (I) with a mixture of aqueous hydrochloric acid and acetone, and isolating the crystalline product. In particular, the crystalline form 1 of hydrochloride salt of compound (I) can be prepared, for example, by stirring the slurry containing compound (I) and a mixture of acetone and aqueous HCl. Equivalent molar amounts of HCl and compound (I) are suitably used. For example, a mixture of acetone and 37% aqueous HCl can be used as a liquid phase. The ratio of acetone to 37% aqueous HCl is can be, for example, from 500:1 to 300:1, for example 400:1. The slurry is suitably stirred at about room temperature for a period sufficient to convert compound (I) to its hydrochloride salt form 1, for example 1-3 days. The crystalline form 1 of hydrochloride salt can be recovered, for example, by filtering and dried at reduced pressure.

The crystalline form 3 of hydrochloride salt of compound (I) can be suitably prepared by contacting compound (I) with a mixture of aqueous hydrochloric acid and ethanol, and isolating the crystalline product. In particular, the crystalline form 3 of hydrochloride salt of compound (I) can be prepared, for example, by stirring the slurry containing compound (I) and a mixture of ethanol and aqueous HCl. Equivalent molar amounts of HCl and compound (I) are suitably used. For example, a mixture of ethanol and 37% aqueous HCl can be used as a liquid phase. The ratio of ethanol to 37% aqueous HCl can be, for example, from 200:1 to 50:1, for example 90:1. The slurry is suitably stirred at about room temperature for a period sufficient to convert compound (I) to its hydrochloride salt form 1, for example from 16 h to 2 days. The crystalline form 3 of hydrochloride salt can be recovered, for example, by filtering and dried at reduced pressure.

The crystalline form 5 of hydrochloride salt of compound (I) can be suitably prepared by grinding any crystalline form of hydrochloride salt of compound (I) in the presense of water, and isolating the crystalline product. Relatively small amounts of water have been found to be sufficient. For example, the weight ratio of water to hydrochloride salt of compound (I) (any crystalline form) of 1:1 has been found suitable. The mixture is suitably grinded, for example in a ball mill, at about room temperature for a period sufficient to convert the initial crystalline form of the hydrochloride salt of compound (I) to crystalline form 5, for example from 15 min to 16 h. The crystalline form 5 of hydrochloride salt can be recovered, for example, by drying the grinded material at reduced pressure.

The crystalline form 8 of hydrochloride salt of compound (I) can be suitably prepared by a method which comprises (i) dissolving compound (I) in a mixture of water and 2-propanol in the presence of hydrochloric acid and formic acid at elevated temperature, (ii) cooling the mixture, and (iii) isolating the crystalline product. In particular, the crystalline form 8 of hydrochloride salt of compound (I) can be prepared by dissolving the compound (I) in a mixture of water and 2-propanol at elevated temperature, for example at 50–70° C., preferably at 55–65° C., in the presence of hydrochloric acid, for example 30% aqueous HCl, and formic acid. The ratio of water to 2-propanol is suitably about 1:1 and the molar amount of HCl is suitably 1.5 equivalents in relation to compound (I). The ratio of formic acid to 30% aqueous HCl is suitably from 15:1 to 10:1, for example 12:1. The solution is suitably filtered while hot. Thereafter more water/2-propanol mixture, suitably again at about 1:1 ratio, can be added while keeping the temperature at 55–65° C. The solution may be optionally seeded if desired. More water/2-propanol mixture, suitably again at about 1:1 ratio, can be again added while keeping the temperature at 55–65° C. The mixture is stirred while allowing it to cool to about room temperature over several hours, for example over 4 to 10 hours. The mixture can be further cooled to 0-10° C. and stirred thereafter for about 1 h. The crystalline form 8 can be isolated, for example by filtering, washed and dried at normal or reduced pressure and elevated temperature, suitably at 40–60° C., for example at 50° C. This method produces crystalline form 8 typically as monohydrate.

Alternatively, crystalline form 8 can be obtained by dissolving compound (I) in tetrahydrofuran and adding acidified ether (1 N HCl in diethyl ether) to the mixture. The precipitated solids are recovered, for example by filtering, and dried, for example, by dry air purge overnight.

The crystalline forms of hydrochloride salt of compound (I) can be formulated into pharmaceutical dosage forms such as tablets, capsules, powders or suspensions together with excipients which are known in the art.

The invention is further illustrated by the following non-limiting examples.

Example 1. Preparation of N-(2',4'-difluoro-5-(5-(1-methyl-1H-pyrazol-4-yl)-1H-benzo[d]imidazol-1-yl)-[1,1'-biphenyl]-3-yl)cyclopropanesulfonamide hydrochloride Crystalline Form 1

200.9 mg of N-(2',4'-difluoro-5-(5-(1-methyl-1H-pyrazol-4-yl)-1H-benzo[d]-imidazol-1-yl)-[1,1'-biphenyl]-3-yl) cyclopropanesulfonamide and 15 ml acetone were combined in a 20 ml vial. To the vial was added 1 ml of acidified acetone (195.9 mg of 37% aqueous HCl mixed with acetone to a total volume of 5 ml). This is approximately 1 equivalent of HCl. The slurry was stirred magnetically at room temperature for 3 days. The resulting solids were recovered by vacuum filtration and stored in a glass vial.

Example 2. Preparation of N-(2',4'-difluoro-5-(5-(1-methyl-1H-pyrazol-4-yl)-1H-benzo[d]imidazol-1-yl)-[1,1'-biphenyl]-3-yl)cyclopropanesulfonamide hydrochloride Crystalline Form 3

2.9995 g of N-(2',4'-difluoro-5-(5-(1-methyl-1H-pyrazol-4-yl)-1H-benzo[d]-imidazol-1-yl)-[1,1'-biphenyl]-3-yl)cyclopropanesulfonamide and 49 ml of absolute ethanol were placed in a 125 ml Erlenmeyer flask. To the flask was added 0.998 ml of acidified ethanol (17.604 g of 37% aqueous HCl mixed with absolute ethanol to a total volume of 30 ml). This is approximately 1 equivalent of HCl. The slurry was stirred magnetically at room temperature overnight. The resulting solids were recovered by vacuum filtration and stored in a glass vial.

Example 3. Preparation of N-(2',4'-difluoro-5-(5-(1-methyl-1H-pyrazol-4-yl)-1H-benzo[d]imidazol-1-yl)-[1,1'-biphenyl]-3-yl)cyclopropanesulfonamide hydrochloride Crystalline Form 5

102.1 mg of N-(2',4'-difluoro-5-(5-(1-methyl-1H-pyrazol-4-yl)-1H-benzo[d]-imidazol-1-yl)-[1,1'-biphenyl]-3-yl) cyclopropanesulfonamide hydrochloride crystalline form 3 was placed in a plastic grind cup followed by 0.1 ml of water. A stainless steel ball was added to the cup. The cup was placed on a Retsch Mill and milled for 20 min at 100% power. The resulting solids were scraped from the grind cup and stored in a glass vial.

Example 4. Preparation of N-(2',4'-difluoro-5-(5-(1-methyl-1H-pyrazol-4-yl)-1H-benzo[d]imidazol-1-yl)-[1,1'-biphenyl]-3-yl)cyclopropanesulfonamide hydrochloride Crystalline Form 8

125.4 mg of N-(2',4'-difluoro-5-(5-(1-methyl-1H-pyrazol-4-yl)-1H-benzo[d]-imidazol-1-yl)-[1,1'-biphenyl]-3-yl) cyclopropanesulfonamide was dissolved in 60 ml of tetrahydrofuran in a beaker. To the beaker was added 248 µl of acidified ether (1 N HCl in diethyl ether). This is approximately 1 equivalent of HCl. Solids precipitated immediately. A dry air purge was run into the beaker overnight. The resulting solids were scraped from the beaker and stored in a glass vial.

Example 5. Preparation of N-(2',4'-difluoro-5-(5-(1-methyl-1H-pyrazol-4-yl)-1H-benzo[d]imidazol-1-yl)-[1,1'-biphenyl]-3-yl)cyclopropanesulfonamide hydrochloride Crystalline Form 8 (Alternative Method)

To an inerted ($N_2$) flask was added water (23.5 ml), 2-propanol (23.5 ml), formic acid (66 ml) and hydrochloric acid (5.21 nil, 30 w-%, 1.5 equivalents). To this solution was added N-(2',4'-difluoro-5-(5-(1-methyl-1H-pyrazol-4-yl)-1H-benzo[d]-imidazol-1-yl)-[1,1'-biphenyl]-3-yl)cyclopropanesulfonamide (18.9 g). The mixture was heated to 60±5° C. The solution was polish filtered while hot. To the filtrate was added 60 ml of 1:1 mixture of water and 2-propanol while keeping the temperature at 60±5° C. The solution was seeded, after which 70 ml more of the 1:1 water/2-propanol mixture was added while keeping the temperature at 60±5° C. The mixture was stirred for 30 min prior to allowing the mixture to cool to 20±5° C. over several hours. The mass was further cooled to 5±5° C. and stirred for 1 h prior to isolation by filtration. The cake was washed with isopropyl alcohol (50 ml) and dried in a vacuum oven at 50° C. to give 17.88 g (93.0%) of crystalline form 8 as a monohydrate.

Example 6. Stability of the Crystalline Forms in Different Water Activity Conditions Stability of the crystalline forms in different water activity conditions was studied in slurry experiments where crystalline forms 1 and 3 were stirred for 3 days at room temperature in mixtures of water and methanol in the presence of HCl to maintain acidic conditions. The results are shown in Table 1.

TABLE 1

Stability of the crystalline forms in different water activity conditions

| Starting material | Solvent[a] | Water activity | Resulting crystalline form |
|---|---|---|---|
| Form 1 | MeOH | 0 | Form 3 |
|  | 4.7% H$_2$O in MeOH | 0.17 | Form 3 |
|  | 10% H$_2$O in MeOH | 0.31 | Form 3 |
|  | 16% H$_2$O in MeOH | 0.44 | Form 3 + Form 8 |
|  | 26.6% H$_2$O in MeOH | 0.59 | Form 3 + Form 8 |
|  | 45.2% H$_2$O in MeOH | 0.75 | Form 8 |
|  | 71.5% H$_2$O in MeOH | 0.88 | Form 5 |
| Form 3 | MeOH | 0 | Form 3 |
|  | 4.7% H$_2$O in MeOH | 0.17 | Form 3 |
|  | 10% H$_2$O in MeOH | 0.31 | Form 3 |
|  | 16% H$_2$O in MeOH | 0.44 | Form 3 + Form 8 |
|  | 26.6% H$_2$O in MeOH | 0.59 | Form 3 + Form 8 |
|  | 45.2% H$_2$O in MeOH | 0.75 | Form 8 |
|  | 71.5% H$_2$O in MeOH | 0.88 | Form 5 |

[a]MeOH is methanol, 80 μl of HCl in MeOH was added to each sample

The results show that crystalline form 3 is favoured under lower water activity conditions (ambient to about 0.3), crystalline form 8 is favoured under mid-range water activity conditions (about 0.4 to about 0.8), and crystalline form 5 is favoured under higher water activity conditions (about 0.9).

Example 7. Long-Term Stability of Forms 3 and 8 at Different Storage Conditions Long-term stability of crystalline forms 3 and 8 at different storage conditions was studied. The conditions were a) 25° C./RH 60% in a closed vessel, b) 40° C./RH 75% in a closed vessel, c) 40° C./RH 75% in an open vessel and d) 25° C./RH 100% in an open vessel. The results are shown in Table 2.

TABLE 2

Long-term stability of forms 3 and 8 at different storage conditions

| Storage condition | Crystalline form 3 | Crystalline form 8 |
|---|---|---|
| 25° C./RH 60% closed | Stable up to 36 months | Stable up to at least 36 months |
| 40° C./RH 75% closed | Stable up to 12 months | Stable up to at least 6 months |
| 40° C./RH 75% open | Change to form 8 after 1 day | Stable up to at least 1 month |
| 25° C./RH 100% open | Change to form 5 after 1 week | Stable up to at least 2 months |

Crystalline form 8 shows good stability at all storage conditions while form 3 changes to form 8 and 5 in open storage conditions 40° C./RH 75% and 25° C./RH 100%, respectively.

Example 8. Hygroscopicity (Dynamic Vapour Sorption)

The hygroscopicity of the crystalline forms 1, 3, 5 and 8 was evaluated using DVS-1 Dynamic Vapour Sorption equipment (Surface Measurement Systems Ltd, London, UK). The amount of 5-10 mg of each crystalline form was equilibrated at 20% RH. The mass change (%) was recorded at 30%, 40%, 50%, 60%, 70%, 80% and 90% RH at T=25° C. The equilibration condition at each point was dm/dt≤0.0003.

The results are presented in FIG. 5. Forms 1, 5 and 8 show particularly low hygroscopicity between 20%-90% RH, form 8 being practically non-hygroscopic.

Example 9. Thermogravimetric Analysis (TGA)

The TGA thermograms for the crystalline forms 1, 3, 5 and 8 were collected on TGA equipment (TA Instruments). The gases recovered during each run were analyzed by head space mass spectroscopy (Agilent GS system). The measurement allowed to register the temperature at which rapid evaporation of Cl ion (disproportionation) started.

The onset temperature of disproportionation for crystalline forms 1, 3, 5 and 8 was determined based on TGA measurements. The results are shown in Table 3. Crystalline form 8 showed highest thermal stability against disproportionation.

TABLE 3

Onset temperature of disproportionation of the crystalline forms

| Crystalline form | Onset temperature of disproportionation (° C.) |
|---|---|
| 1 | 148 |
| 3 | 171 |
| 5 | 145 |
| 8 | 187 |

The invention claimed is:

1. A compound which is hydrochloride salt of N-(2',4'-difluoro-5-(5-(1-methyl-1H-pyrazol-4-yl)-1H-benzo[d]imidazol-1-yl)-[1,1'-biphenyl]-3-yl)cyclopropanesulfonamide (I), wherein the compound is in crystalline form.

2. The compound according to claim 1, wherein the compound is in crystalline form 1 and is characterized by a X-ray powder diffraction pattern comprising peaks at about 4.6, 9.6, 18.7, 19.2, 23.5, 25.0 and 26.9 degrees 2-theta.

3. The compound according to claim 1, wherein the compound is in crystalline form 3 and is characterized by a X-ray powder diffraction pattern comprising peaks at about 7.2, 9.2, 11.6, 16.1, 18.5, 25.9 and 27.9 degrees 2-theta.

4. The compound according to claim 1, wherein the compound is in crystalline form 5 and is characterized by a X-ray powder diffraction pattern comprising peaks at about 8.3, 9.5, 18.5, 19.8, 21.1, 23.9, 25.1 and 27.4 degrees 2-theta.

5. The compound according to claim 1, wherein the compound is in crystalline form 8 and is characterized by a X-ray powder diffraction pattern comprising peaks at about 4.7, 14.2, 16.1, 18.0, 21.2, 23.5 and 26.5 degrees 2-theta.

6. The compound according to claim 5, wherein the crystalline form is a monohydrate.

7. A method of preparing a compound according to claim 2, comprising combining N-(2',4'-difluoro-5-(5-(1-methyl-1H-pyrazol-4-yl) -1H-benzo[d]imidazol-1-yl)-[1,1'-biphenyl]-3-yl)cyclopropanesulfonamide with a mixture of aqueous hydrochloric acid and acetone, and isolating the crystalline product.

8. A method of preparing a compound according to claim 3, comprising combining N-(2',4'-difluoro-5-(5-(1-methyl-1H-pyrazol-4-yl) -1H-benzo[d]imidazol-1-yl)-[1,1'-biphenyl]-3-yl)cyclopropanesulfonamide with a mixture of aqueous hydrochloric acid and ethanol, and isolating the crystalline product.

9. A method of preparing a compound according to claim 4, comprising grinding any crystalline form of hydrochloride salt of N-(2',4'-difluoro-5-(5-(1-methyl-1H-pyrazol-4-yl)-1H-benzo[d]imidazol-1-yl)-[1,1'-biphenyl]-3-yl)cyclopropanesulfonamide in the presence of water, and isolating the crystalline product.

10. A method of preparing a compound according to claim 5, comprising:
 (i) dissolving N-(2',4'-difluoro-5-(5-(1-methyl-1H-pyrazol-4-yl)-1H-benzo[d]imidazol-1-yl)-[1,1'-biphenyl]-3-yl)cyclopropanesulfonamide in a mixture of water and 2-propanol in the presence of hydrochloric acid and formic acid at elevated temperature,
 (ii) cooling the mixture, and
 (iii) isolating the crystalline product.

11. A pharmaceutical dosage form comprising a compound according to claim 1 and an excipient.

12. A method of treatment of treating cancer characterized by abnormal FGFR signalling, comprising administering a therapeutically effective amount of the compound according to claim 1 to a subject in need thereof.

13. The method according to claim 12, wherein the cancer is multiple myeloma, gastric cancer, endometrial cancer, prostate cancer, breast cancer, cholangiocarcinoma, or uroepithelial carcinoma.

14. A method of preparing a compound according to claim 6, comprising:
 (i) dissolving N-(2',4'-difluoro-5-(5-(1-methyl-1H-pyrazol-4-yl)-1H-benzo[d]imidazol-1-yl)-[1,1'-biphenyl]-3-yl)cyclopropanesulfonamide in a mixture of water and 2-propanol in the presence of hydrochloric acid and formic acid at elevated temperature,
 (ii) cooling the mixture, and
 (iii) isolating the crystalline product.

\* \* \* \* \*